(12) United States Patent
Kurata et al.

(10) Patent No.: US 7,871,519 B2
(45) Date of Patent: Jan. 18, 2011

(54) METHODS FOR DETECTION, IDENTIFICATION AND QUANTIFICATION OF IMPURITIES

(75) Inventors: Christine Kurata, LaJolla, CA (US); Daniel Capaldi, Carlsbad, CA (US); Zhiwei Wang, Carlsbad, CA (US); Nhuy Luu, Vista, CA (US); Hans-joachim Gaus, Carlsbad, CA (US); Claus André Frank Rentel, San Marcos, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 439 days.

(21) Appl. No.: 11/910,057

(22) PCT Filed: Mar. 31, 2006

(86) PCT No.: PCT/US2006/012042

§ 371 (c)(1),
(2), (4) Date: Jun. 13, 2008

(87) PCT Pub. No.: WO2006/107775

PCT Pub. Date: Oct. 12, 2006

(65) Prior Publication Data

US 2009/0095896 A1 Apr. 16, 2009

Related U.S. Application Data

(60) Provisional application No. 60/667,592, filed on Apr. 1, 2005.

(51) Int. Cl.
*B01D 15/08* (2006.01)

(52) U.S. Cl. .................. 210/635; 210/656; 210/198.2; 73/61.52; 435/6; 536/25.4

(58) Field of Classification Search ................. 210/635, 210/656, 659, 198.2; 73/61.52; 435/6; 536/23.1, 536/25.4
See application file for complete search history.

(56) References Cited

U.S. PATENT DOCUMENTS 6,024,878 A * 2/2000 Gjerde et al. ............... 210/635

(Continued)

FOREIGN PATENT DOCUMENTS

WO WO 01/55713 8/2001

OTHER PUBLICATIONS

Apffel et al., "Analysis of Oligonucleotides by HPLC—Electrospray Ionization Mass Spectrometry" Anal. Chem. (1997) 69:1320-1325.

(Continued)

*Primary Examiner*—Ernest G Therkorn
(74) *Attorney, Agent, or Firm*—Woodcock Washburn LLP

(57) ABSTRACT

Provided is a method comprising introducing a sample comprising a plurality of oligonucleotides into an ion pair high performance liquid chromatography column having a buffered mobile phase and allowing at least a portion of the oligonucleotides to separate; allowing the oligonucleotides to elute from the column; and introducing the oligonucleotides into a mass spectrometer and quantifying at least a portion of the oligonucleotides by mass spectrometry. In the method, at least a portion of the oligonucleotides are co-eluting oligonucleotides that differ in mass by no more than 20%; and the buffered mobile phase causes at least 50 mole percent of co-eluting oligonucleotides to have the same charge when they enter the mass spectrometer.

22 Claims, 9 Drawing Sheets

Interpreting ion currents as effective volumes of injection using a quadratic calibration curve

U.S. PATENT DOCUMENTS

2002/0088753 A1* 7/2002 Huber et al. ............... 210/656
2005/0011836 A1* 1/2005 Bidlingmeyer et al. ...... 210/656
2006/0040308 A1* 2/2006 Capaldi et al. ............... 435/6

OTHER PUBLICATIONS

Apffel et al., "New procedure for the use of high-performance liquid chromatography-electrospray ionization mass spectrometry for the analysis of nucleotides and oligonucleotides" J. Chromatogr. (1997) 777:3-21.

Beverly, et al., "Liquid chromatography/electrospray mass spectrometric analysis of metabolites from an inhibitory RNA duplex" Rapid Comm. Mass Spec. (2005) 19:1675-1682.

Beverly et al., "Liquid chromatography electrospray ionization mass spectrometry analysis of the ocular metabolites from a short interfering RNA duplex" J. Chromatogr. (2006) 835:62-70.

Bothner et al., "Liquid Chromatography Mass Spectrometry of Antisense Oligonucleotides" Bioorg. Med. Chem. Lett. (1995) 5:2863-2868.

Cheng et al., "Charge State Reduction of Oligonucleotide Negative Ions from Electrospray Ionization" Anal. Chem. (1995) 67:586-593.

Covey et al., "The Determination of Protein, Oligonucleotide and Peptide Molecular Weights by Ion-spray Mass Spectrometry" Rapid. Comm. Mass Spec. (1988) 2:240-256.

Dai et al., "Characterization and quantification of Bcl-2 antisense G3139 and metabolites in plasma and urine by ion-pair reversed phase HPLC coupled with electrospray ion-trap mass spectrometry" J. Chromatogr. (2005) 825:201-213.

Gaus et al., "On-Line HPLC Electrospray Mass Spectrometry of Phosphorothioate Oligonucleotide Metabolites" Anal. Chem. (1997) 69:313-319.

Gilar, "Analysis and Purification of Synthetic Oligonucleotides by Reversed-Phase High-Performance Liquid Chromatography with Photodiode Array and Mass Spectroemtry Detection" Analytical Biochemistry (2001) 298:196-206.

Greig et al., "Utility of Organic Bases for Improved Electrospray Mass Spectrometry of Oligonucleotides" Rapid Comm. Mass Spec. (1995) 9:97-102.

Greig et al., "Negative Ionization Micro Electrospray Mass Spectrometry of Oligonucleotides and their Complexes" Rapid. Comm. Mass Spec. (1996) 10:47-50.

Griffey et al., "Characterization of Oligonucleotide Metabolism In Vivo via Liquid Chromatography/Electrospray Tandem Mass Spectrometry with a Quadrupole Ion Trap Mass Spectrometer" J. Mass Spec. (1997) 32:305-313.

Huber et al., "On-Line Cation Exchange for Suppression of Adduct Formation in Negative-Ion Electrospray Mass Spectrometry of Nucleic Acids" Anal. Chem. (1998) 70:5288-5295.

Huber et al., "Analysis of Nucleic Acids by Capillary Ion-Pair Reversed-Phase HPLC Coupled to Negative-Ion Electrospray Ionization Mass Spectrometry" Anal. Chem. (1999) 71:3730-3739.

Huber et al., "Sheath liquid effects in capillary high-performance liquid chromatography-electrospray mass spectrometry of oligonucleotides" J. Chromatogr. (2000) 870:413-424.

International Search Report for PCT/US06/12042 dated Aug. 16, 2006.

Keough et al., "Detailed Characterization of Antisense DNA Oligonucleotides" Anal. Chem. (1996) 68:3405-3412.

McLuckey et al., "Tandem Mass Spectrometry of Small, Multiply Charged Oligonucleotides" J. Am. Mass Spectrom. (1992) 3:60-70.

McLuckey et al., "Ion Trap Tandem Mass Spectrometry Applied to Small Mulitply Charged Oligonucleotides with a Modified Base" J. Am. Mass Spectrom. (1994) 5:740-747.

Premstaller et al., "High-Performance Liquid Chromatography—Electrospray Ionization Mass Spectrometry of Single- and Double-Stranded Nucleic Acids Using Monolithic Capillary Columns" Anal. Chem. (2000) 72:4386-4393.

Tengvall et al., "Characterization of antisense oligonucleotide-peptide conjugates with negative ionization electrospray mass spectrometry and liquid chromatography-mass spectrometry" J. Pharm. Biomed. Anal. (2003) 32:581-590.

Fountain et al., "Purification of dye-labeled oligonucleotides by ion-pair reversed-phase high-performance liquid chromatography" Journal of Chromatography B: Biomedical Sciences & Applications (2003) 783(1):61-72.

Griffey et al., "Oligonucleotide charge states in negative ionization electrospray-mass spectrometry area function of solution ammonium ion concentration" Journal of the American Society for Mass Spectrometry (1997) 8(2):155-160.

Supplementary European Search Report for application No. 06740257.8 dated Aug. 19, 2010.

* cited by examiner

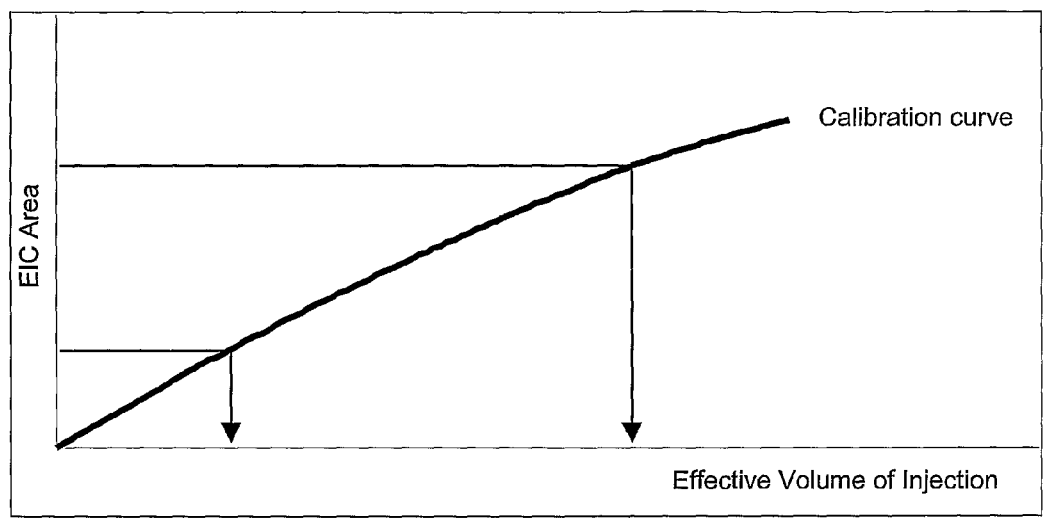
Figure 1. Interpreting ion currents as effective volumes of injection using a quadratic calibration curve

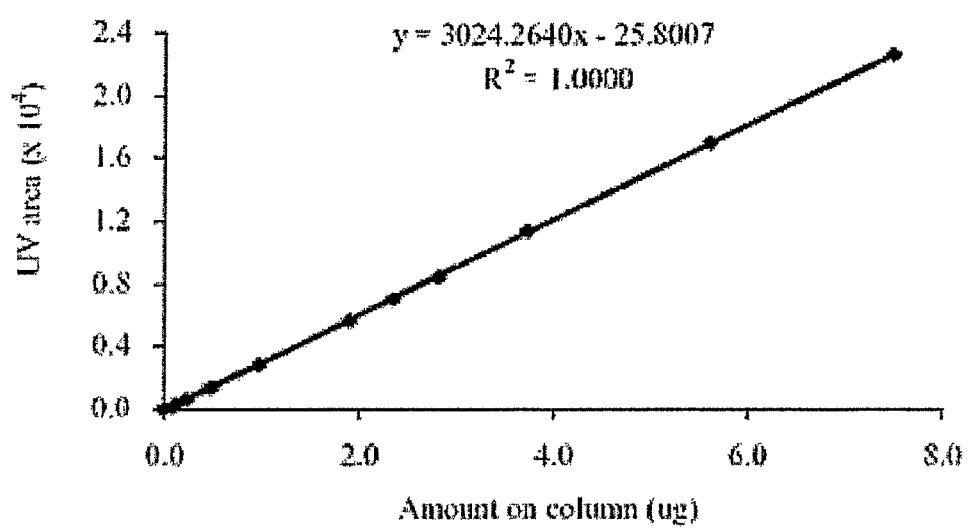
Figure 2. Plot of UV Response Against Column Load For Main Peak

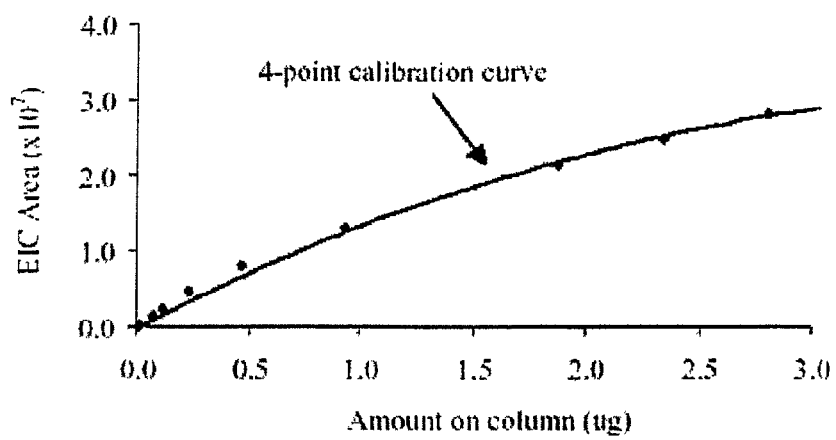
Figure 3. Plot Of Ion Current Against Column Load For A 20 Nucleotide 5-10-5 2'-O-Methoxyethyl Gapmer.

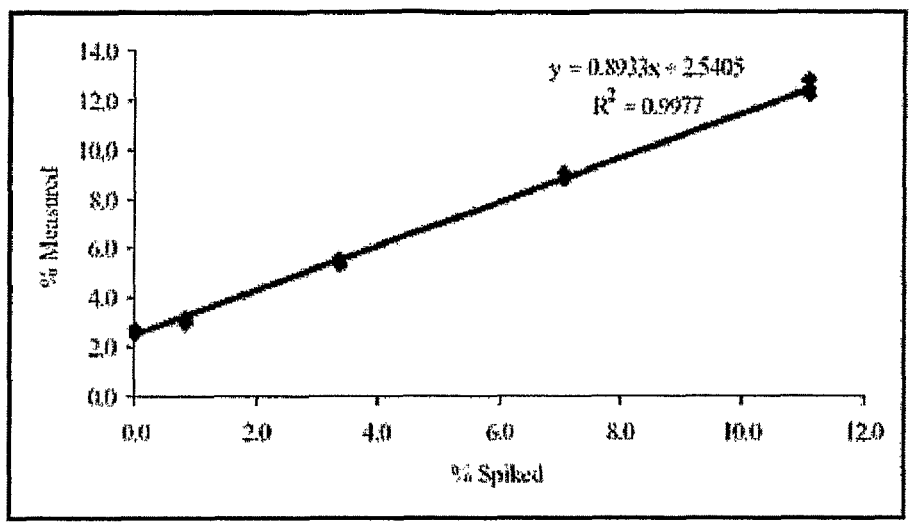
Figure 4. Graph Of Amount Recovered Against Amount Spiked For Impurity 1.

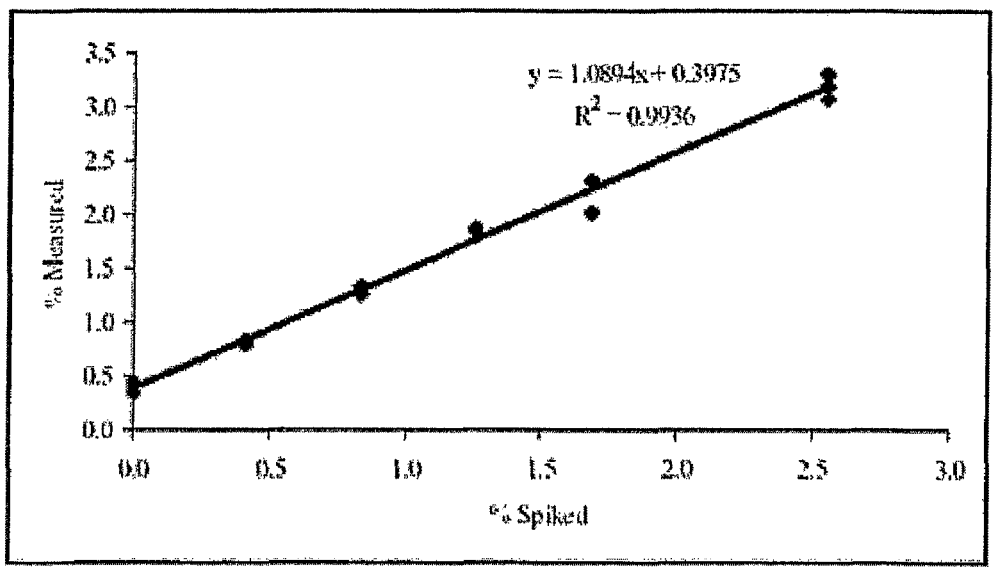
Figure 5. Graph Of Amount Recovered Against Amount Spiked For Impurity 2

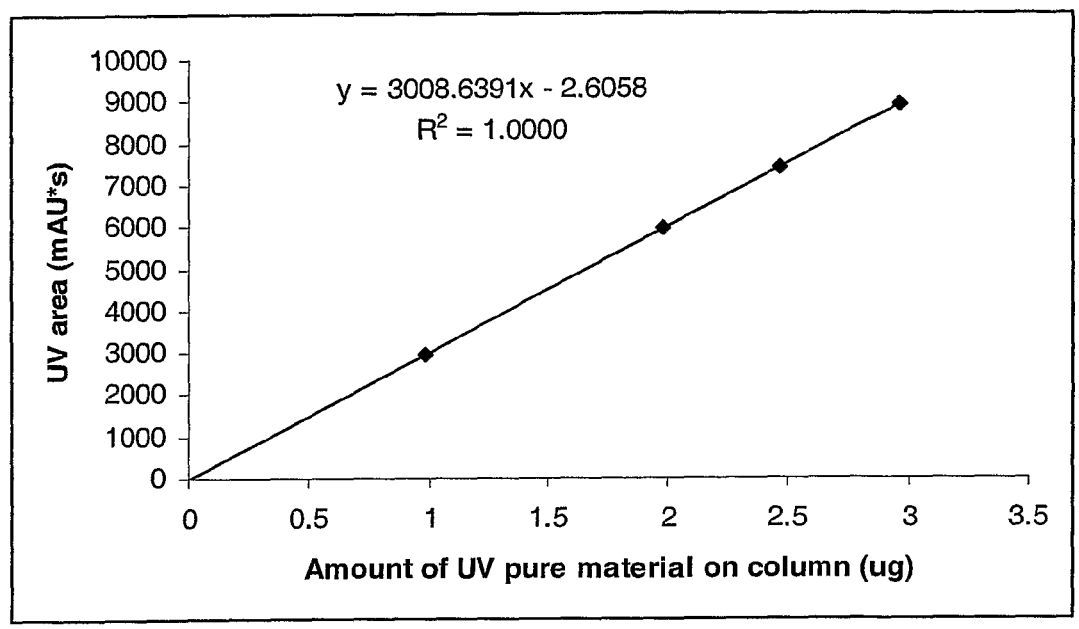
Figure 6. Plot of UV Absorbance Against Amount Of UV Pure Material On Column For The Reference Standard

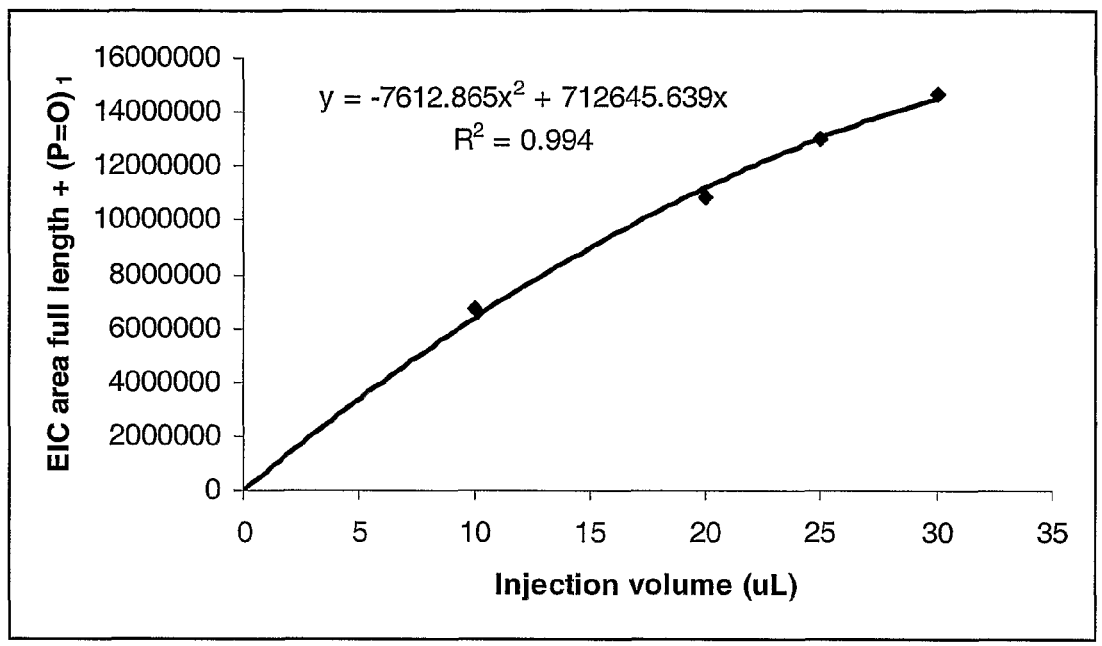
Figure 7. Plot Of Extracted Ion Current (EIC) Area For The Full-Length Fully Thioated (n) And $(P=O)_1$ Components Against Injection Volume For The Reference Standard

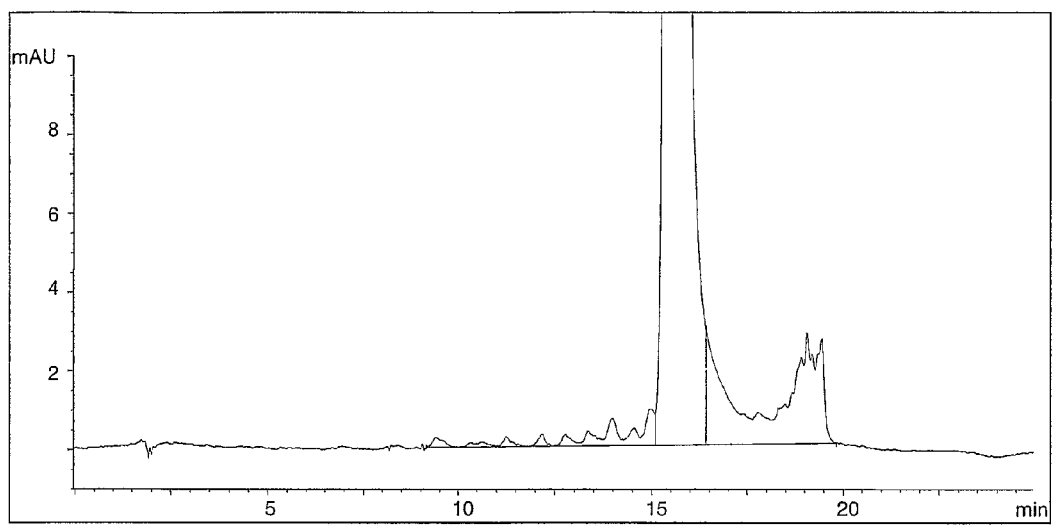
Figure 8: UV Chromatogram Of The First Injection Of A 20 Nucleotide 5-10-5 2'-O-Methoxyethyl Gapmer.

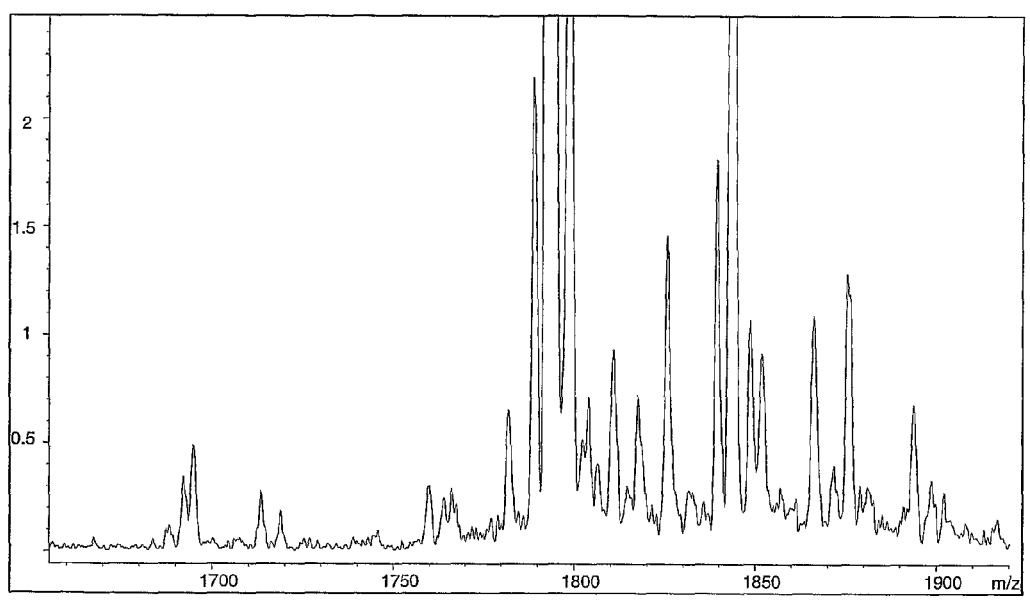
Figure 9 Average Mass Spectrum Of The Main UV Peak Of The First Iinjection Of A 20 Nucleotide 5-10-5 2'-O-Methoxyethyl Gapmer.

METHODS FOR DETECTION, IDENTIFICATION AND QUANTIFICATION OF IMPURITIES

CROSS-REFERENCE TO RELATED APPLICATIONS

This application is the 371 National Stage of International Application No. PCT/US2006/012042 filed Mar. 31, 2006, which claims the benefit of U.S. Provisional Application No. 60/667,592, filed Apr. 1, 2005, the disclosure of which is incorporated herein by reference in its entirety.

FIELD OF THE INVENTION

The present invention provides methods for the detection, identification and quantification of impurities in a sample, using Ion Pair-High Performance Liquid Chromatography-Ultra Violet-Mass Spectrometry analysis.

BACKGROUND

Presently practiced methods for the separation and quantification of oligonucleotide samples have several significant limitations. First, oligonucleotides are polyanionic species. In almost all HPLC-MS applications, e.g., electrospray ionization (ESI) systems employing hexafluoroisopropyl alcohol, the signal due to the oligonucleotide is divided among several different charge states. This males detection and quantitation, especially of impurities that are present at low levels, challenging because the signal-to-noise for each individual charge state is reduced. If one chooses to quantitate over multiple charge states, the method quickly becomes complicated and difficult to use for routine quality control (QC) use.

A second important consideration when using mass spectrometry for quantitative oligonucleotide analysis is that molecules of different lengths can have very different ionization efficiencies. Shorter oligonucleotides often ionize with much greater efficiency than longer oligonucleotides. This makes quantitation of a mixture of oligonucleotides of varying lengths by mass spectrometry difficult because one must determine the relative ionization efficiencies beforehand.

Thirdly, unlike the UV response of oligonucleotides, which obeys Beer's law at analytically relevant concentrations, the mass spectral response in ESI-MS across the same concentration range is not linear. This is believed to be due to ion suppression. In essence, at high oligonucleotide concentrations there is insufficient space on a single electrospray droplet to accommodate in a linear fashion more and more molecules for ionization. This results in a plateauing of the response at higher concentrations.

There is a need in the art for improved methods of separation and quantification of oligonucleotides.

SUMMARY

In some embodiments, the invention concerns a method comprising:

introducing a sample comprising a plurality of oligonucleotides into high performance liquid chromatography column having a buffered ion-pair mobile phase and allowing at least a portion of the oligonucleotides to separate;

allowing the oligonucleotides to elute from the column; and introducing the oligonucleotides into a mass spectrometer and quantifying at least a portion of the oligonucleotides by mass spectrometry. Preferably, at least a portion of the oligonucleotides are co-eluting oligonucleotides that differ in mass by no more than 20%. Preferably, the buffered mobile phase causes at least 50 mole percent of co-eluting oligonucleotides to have the same charge when they enter the mass spectrometer.

In certain embodiments, the method additionally comprises detecting oligonucleotides with UV detection before they enter the mass spectrometer.

In some embodiments, the oligonucleotides differing by 20 mass percent or less are quantified by mass spectrometry and those differing by more than 20 mass percent are quantified by their UV spectra.

Co-eluting oligonucleotides can be quantified by mass spectrometry, where the quantification comprises utilization of a calibration curve obtained by a plot of mass spectral response versus the amount of a sample oligonucleotide injected into the mass spectrometer to determine the amount of the individual oligonucleotides.

In some embodiments, the buffered mobile phase has a pH from about 6 to about 8. In certain embodiments, the buffered mobile phase comprises a bulky amine and an acid. One preferred bulky amine is a trialkylamine. Suitable trialklylamines include tripropylamine, tributylamine, tripentylamine, trihexylamine, dimethylhexylamine, dimethyloctylamine, and diethylbutylamine. In some preferred embodiments, the bulky amine is tributylamine.

In some embodiments, the acid is acetic acid, formic acid, propionic acid, trifluoracetic acid or carbonic acid. In certain embodiments, it is preferred to use acetic acid.

Some methods have at least 50 mole percent of the co-eluting oligonucleotides are in the $-1$, $-2$, $-3$, $-4$, $-5$, or $-6$ charge state. Some methods have at least 50 mole percent of the co-eluting oligonucleotides are in the $-3$, $-4$, or $-5$ charge state. In certain embodiments, at least 70 mole percent of the co-eluting oligonucleotides are in the $-4$ charge state.

In some embodiments, the oligonucleotides comprise single strand or double strand oligonucleotides. Certain methods have at least one oligonucleotide comprises at least one chemical modification. Chemical modifications can comprise at least one of a modified base, a modified sugar, a modified internucleoside linkage or a conjugate group linked to the oligonucleotide. Some preferred co-eluting oligonucleotides are of lengths selected from the following ranges 12 to 30, 15 to 25 or 19 to 21 nucleobases.

In some embodiments, at least one oligonucleotide is a drug substance.

In certain embodiments, the co-eluting oligonucleotides comprise a target oligonucleotide and one or more of the impurities selected from the target oligonucleotide missing one nucleotide, the target oligonucleotide missing one nucleoside, the target oligonucleotide missing one purine base (with or without the addition of methanol or water), the target oligonucleotide missing one pyrimidine base (with or without the addition of methanol or water), the target oligonucleotide containing an additional nucleotide, the target oligonucleotide containing an additional ethylenephosphorothioate group, the target oligonucleotide containing an additional trichlorethanol group or the target oligonucleotide containing an additional cyanoethyl group.

In some embodiments, the target oligonucleotide has 12-30, 15-25, 18-24, or 19 to 21 nucleotides. In some embodiments, the target oligonucleotide has 19, 20, or 21 nucleotides.

Some methods use a common calibration curve for the quantification of the co-eluting oligonucleotides.

BRIEF DESCRIPTION OF THE DRAWINGS

FIG. 1 illustrates interpreting ion currents as effective volumes of injection using a quadratic calibration curve.

FIG. 2 presents a plot of UV response against column load for the main peak.

FIG. 3 is a plot of ion current against column load for a 20 nucleotide 5-10-5 2'-O-methoxyethyl gapmer.

FIG. 4 is a graph of amount recovered against amount spiked for Impurity 1.

FIG. 5 is a graph of amount recovered against amount spiked for Impurity 2.

FIG. 6 presents a plot of UV absorbance against amount of UV pure material on column for the reference standard.

FIG. 7 is a plot of extracted ion current (EIC) area for the full-length fully thioated (n) and $(P=O)_1$ components against injection volume for the reference standard.

FIG. 8 shows a UV chromatogram of the first injection of a 20 nucleotide 5-10-5 2'-O-methoxyethyl gapmer drug substance.

FIG. 9 represents an average mass spectrum of the main UV peak of the first injection of a 20 nucleotide 5-10-5 2'-O-methoxyethyl gapmer drug substance.

DETAILED DESCRIPTION

The assay, identity and impurity profile of oligonucleotides can be determined by ion-pair high performance liquid chromatography with ultra violet and electrospray ionization mass spectrometry detection (IP-HPLC-UV-MS). Identity is confirmed by mass spectrometric detection of the appropriate molecular ion as the main component of the sample. Assay is performed by weight-based assay against a standard of known purity using IP-HPLC with detection by UV absorption. The IP-HPLC-UV method does not have complete specificity; therefore, all species that elute within the main peak are quantitated by mass spectrometry. The weight-based assay as determined by UV absorption is then corrected for the presence of other species within the main peak. The impurity profile of the sample is determined by the same IP-HPLC method with detection by UV absorption and MS. Those species that elute within the main peak are detected by ion-current and are quantitated by adjusting for the UV purity of the sample as described above.

There are several features of the above system in regard to the analysis of oligonucleotides that are worthy of comment. Firstly, oligonucleotides are polyanionic species. In almost all HPLC-MS applications, e.g., electrospray ionization (ESI) systems employing hexafluoroisopropyl alcohol, the signal due to the oligonucleotide is divided among several different charge states. This makes detection and quantitation, especially of impurities that are present at low levels challenging because the signal-to-noise for each individual charge state is reduced. If one chooses to quantitate over multiple charge states, the method quickly becomes complicated and, in our opinion, unsuitable for routine QC use. The analytical methods described herein address the issue by developing a buffer system that forces most of the oligonucleotide into a single charge state, thereby greatly increasing signal-to-noise for a given sample load. In some systems, oligonucleotides containing 19 to 21 nucleobases in length are mostly (>70%) quadruply charged.

A second important consideration when using mass spectrometry for quantitative oligonucleotide analysis is that molecules of different lengths can have very different ionization efficiencies. Shorter oligonucleotides often ionize with much greater efficiency than longer oligonucleotides. This makes quantitation of a mixture of oligonucleotides of varying lengths by mass spectrometry difficult because one must determine the relative ionization efficiencies beforehand. The analytical methods described herein address the issue by using IP-HPLC to separate shorter and longer oligonucleotide impurities from the parent sequence prior to mass spectrometry quantitation. As mentioned above, these components are quantitated by UV detection. Impurities that co-elute with the parent sequence, and are quantitated by mass spectrometry, have lengths that are within one nucleotide of the parent sequence. We have demonstrated through recovery experiments that ionization efficiencies for these components and the parent sequence are, for all practical purposes, identical.

The concentration of the ion-pair buffer was selected carefully to provide a balance between chromatographic separation and mass spectral sensitivity. Higher ion-pair buffer concentrations increase chromatographic separation but reduce the mass spectral response significantly thereby making detection and quantitation of low level impurities more difficult.

Thirdly, unlike the UV response of oligonucleotides, which obeys Beer's law at analytically relevant concentrations, the mass spectral response in ESI-MS across the same concentration range is not linear. This is believed to be due to ion suppression. In essence, at high oligonucleotide concentrations there is insufficient space on a single electrospray droplet to accommodate in a linear fashion more and more molecules for ionization. This results in a plateauing of the response at higher concentrations. Although the ion-pair system used in our method does not resolve species that are quantitated by mass spectrometry from each other to a chromatographically useful extent, there is resolution enough between the different components of the main peak such that they enter the mass spectrometer at different times. This means that the total number of molecules on a solvent droplet at the time the n−1 components (the n−1 component is a family of oligonucleotides that are one nucleotide shorter than the parent molecule), for example, enter the mass spectrometer is less than the total number of molecules on a droplet when the full-length fully thioated component enters the mass spectrometer. This in turn means the latter suffers more ion suppression than the former. This situation is repeated with all components that are quantitated by mass spectrometry except the $(P=O)_1$ component (the $(P=O)_1$ component is a family of oligonucleotides that contain one phosphate diester linkage), which coelutes exactly with the full-length fully thioated species. If this effect is not accounted for, a direct comparison of the extracted ion current (EIC) areas due to two components present at different amounts leads one to overestimate the relative amount of the lesser component.

The fact that the mass spectral response does not vary linearly with sample concentration does not preclude mass spectrometry as a means for quantitation. Instead, all that is required for quantitation is a way to describe the relationship accurately. In this regard, we have demonstrated that the relationship between mass spectral response and sample load is described accurately by a quadratic equation. We use this knowledge to interpret the extracted ion currents due to the individual components of the sample in the following manner: Firstly, a calibration curve is established by injecting various volumes of a standard solution of oligonucleotide. The extracted ion currents due to the full-length, fully thioated (n) and the $(P=O)_1$ components for each injection, for example, can be summed and plotted against injection volume. A quadratic equation is then fit to these points. The individual extracted ion currents due to the various impurities in the sample and, because they coelute exactly, the sum of the extracted ion currents due to the n and the $(P=O)_1$ components, are projected onto the x-axis as "effective volumes of injection." This procedure is illustrated graphically in FIG. 1.

The effective volumes of injection, which are in essence linearized mass spectral responses, are summed and the relative amounts of each impurity, and the sum of the n and the $(P=O)_1$ components, calculated. The individual contributions of the n and $(P=O)_1$ components are established by multiplying their summed effective volume of injection by the respective decimal fractions of their individual extracted ion currents to the sum of these values.

Co-eluting species which may be detected and quantified via the methods of the present invention include impurities described in United States Patent Application No. 20060040308 filed Aug. 22, 2005, which is herein incorporated by reference in its entirety.

The method of the present invention is useful, for example, in the analysis of drug substance, drug substance in aqueous solution (drug product) and lyophilized drug product. In conjunction with appropriate sample preparation procedures, this method may also be applicable for the analysis of other drug product presentations, such as enemas and solid oral dosage forms.

The invention is illustrated by the methods discussed in the following paragraphs.

1. Sampling

Sampling protocols are shown by the following examples that are intended to be illustrative not limiting.

Drug substance release and stability testing may be performed, for example, on two preparations of each sample. Each preparation is injected once into the IP-HPLC-MS system. The mass spectral and UV data of the first injection is analyzed to provide the reportable value for impurity profile. The peak area of the main UV peak of the second injection is determined. The peak areas of the main UV peak of both injections can be corrected for co-eluting components using the same mass spectral impurity profile to give two estimates of the assay value. The individual values can be averaged to provide the reportable value for assay.

Drug product release (without the requirement for content uniformity) and stability testing may be performed on two preparations of each sample. Test articles may be combined to provide sufficient sample for analysis. Each preparation is injected once into the IP-HPLC-MS system. The mass spectral and UV data of the first preparation can be analyzed to provide the reportable value for impurity profile. The peak area of the main UV peak of the second preparation is determined. The peak areas of the main UV peak of both preparations are corrected for co-eluting components using the same mass spectral impurity profile to give two estimates of label claim. The individual values are averaged to provide the reportable value for label claim.

Content uniformity (if applicable) may be assessed at release by analysis of the prescribed number of test articles. The UV data for each preparation is analyzed. The mass spectral and UV data of the first preparation are analyzed to provide the reportable value for impurity profile. The peak area of the main UV peak of the second preparation is determined. The peak areas of the main UV peak of both preparations are corrected for co-eluting components using the same mass spectral impurity profile to give two estimates of label claim. The individual values are averaged to provide the reportable value for label claim. The remaining data points are used to determine content uniformity. The criterion for content uniformity is peak area of the main UV peak.

2. Equipment and Equipment Parameters

Equipment and their parameters are illustrated in the following paragraphs. One skilled in the art will realize that other equipment and different parameters may be used.

Equipment used in the method can include:
a five-place analytical balance;
a YMC ODS-AQ HPLC column 3-um particle size, 200-A pore size, 2×150 mm column dimension, or equivalent; and
a gradient HPLC instrument with variable wavelength UV detector and auto sampler, interfaced to an electrospray mass spectrometer with data processing system (Agilent 1100 HPLC-MSD, or equivalent).

Method conditions include:
a detector wavelength: 260 nm (4-nm bandwidth)
a reference wavelength (if applicable): 400 nm (80-nm bandwidth);
a column temperature: 50° C.;
data acquisition time of 25 minutes;
an equilibration time of 10 minutes;
a total run time of 35 minutes
a gradient as shown in the table below:

| Time (minutes) | Flow Rate (mL/min) | Eluent Composition (%) | |
|---|---|---|---|
| | | Eluent A | Eluent B |
| 0 | 0.25 | 55 | 45 |
| 22 | 0.25 | 20 | 80 |
| 25 | 0.25 | 20 | 80 |
| 26 | 0.25 | 55 | 45 |
| 35 | 0.25 | 55 | 45 |

Mass spectrometer settings for the Agilent 1100 MSD (settings may vary for other instruments) can be as shown below. It should be noted that the mass range is set to extend, to the nearest 0.1 m/z, from 150 m/z below to 150 m/z above the signal due to the given charge state of the most abundant mass of the full-length, target oligonucleotide.

| Parameter | Setting |
|---|---|
| Mass range | from 150 m/z below to 150 m/z above the signal due to the given charge state of the most abundant mass of the full-length, target oligonucleotide. |
| Scan mode | Negative Polarity |
| Ionization mode | API-ES |
| Needle voltage | 4000 V |
| Nebulizer pressure | 25 ± 5 psig |
| Drying gas flow | 12 L/min |
| Drying gas temperature | 275° C. |
| Fragmentor voltage | 100 V |
| Gain | 2 |
| Threshold | 50 |
| Step size [amu] | 0.1 |
| Data acquisition time | 2-25 minutes |
| Data storage | Full |
| Peak width | 0.12 mins |

3. Reagents and Materials

In some embodiments, suitable reagents and materials include:
tributylamine (Fluka #90781 or equivalent);
glacial acetic acid (Mallinkrodt #2504 or equivalent);

HPLC grade bottled water (Baker #4218-03 or equivalent)—bottled HPLC water is typically used for the preparation of mobile phases in order to minimize baseline noise in the mass spectrum and to maximize sensitivity;

acetonitrile (HPLC grade);

ethylenediaminetetraacetic acid (Fluka #03609 or equivalent);

argon gas (High purity grade); and aluminum weigh pan, (VWR #34107-052, or equivalent).

Other materials of suitable properties and purity may be used in the practice of the invention.

4. System Suitability Testing

In one embodiment, the following stability requirements, referred to herein by the number (4.1-4.6) listed below, can be utilized. In some embodiments, the retention time of the main UV peak of all reference standard injections should typically be between from about 12 to about 22 minutes.

4.1: The relative standard deviation (RSD) of the main UV peak area of the three 25-uL injections of the reference standard bracketing the samples should be less than 2.0%.

4.2: The average UV purity of the three 25-uL injections of reference standard bracketing the samples should be within 1% of the assigned value.

4.3: The mass of the main component of the main UV peak of the three 25-uL injections of reference standard bracketing the samples should be within 0.2 amu of the calculated most abundant signal (rounded to 1 decimal place) due to the given charge state of the full-length, target oligonucleotide.

4.4: A plot of the area of the main UV peak against the amount (in ug) of UV-pure standard on column for the 10, 20, 30 and the first 25-uL injection of the reference standard should be linear ($R^2 \geq 0.995$).

4.5: The data obtained by plotting the extracted ion currents (EICs) due to the given charge of the main component and its major impurity against injection volume for the 10, 20, 30 and the first 25-uL injection of the reference standard should be fit by a second-order polynomial expression. The correlation factor $R^2$ should be $\geq 0.99$.

4.6: If using a solid reference material, the response factors calculated below should be within 2.0% of each other.

5. Preparation of Standards

Preparation of standards is illustrated by the following examples.

A standard in aqueous solution, at a known concentration of approximately 0.1 mg/mL, can be made available in pre-filled vials. An aliquot of solution should be transferred to the appropriate HPLC injection vial.

If pre-filled standard vials are not available, a standard can be prepared and checked by a characterized batch of the relevant drug substance using the sample preparation guidelines described in the Drug Substance section in Preparation of Samples below. An aliquot of solution can be transferred to the appropriate HPLC injection vial. It should be noted that by definition, no suitable standard will be available for the initial analysis of a new drug substance candidate. In this case it is acceptable to use the sample solution itself to perform appropriate system suitability tests and to generate a standard curve. An assay value is typically not generated from this analysis.

6. Preparation of Samples

Sample preparation is illustrated below. One skilled in the art will recognize that modifications to these procedures can be made so long as the sample is suitable for analysis on the equipment utilized.

The sample should be homogeneous and equilibrated to ambient temperature and humidity prior to weighing. Samples should be equilibrated for a minimum of 4 hours. An analytical balance can be used to weigh accurately (to within 0.1 mg) 30±2 mg of drug substance onto weighing paper or a weigh boat. The sample is transferred into a 250-mL volumetric flask and fill to the mark with bottled HPLC or deionized water. In some embodiments the sample is mixed by using a vortex or the mixing is accomplished by inversion. An aliquot can be transferred to an HPLC injection vial. A duplicate sample is desirably prepared in an identical fashion. The time and date when the samples were diluted are typically recorded. Material is also weighed for water determination. If residual solvents and sodium acetate have not already been determined, the material can be weighed for these analyses as required by the appropriate method.

Solution Formulations

Illustrative solution formulation techniques are presented in the following paragraphs.

Using "to contain" pipettes, with rinsing to ensure quantitative transfer from the pipette, each of the duplicate drug product samples can be diluted with HPLC or deionized water to a concentration of approximately 0.1 mg/mL. Vials may be pooled to provide adequate volume. An aliquot of solution can be transferred to the appropriate HPLC injection vial.

Highly viscous samples may be difficult to pipette. For such samples more accurate results may be obtained by weighing the amount of sample transferred. Knowledge of the sample density is required.

The sample is typically used at room temperature. In duplicate, one can transfer not less than 50 mg of sample to an aluminum weigh boat and record the weight. The pan and its contents can be placed in a suitably sized volumetric flask such that the sample concentration following dilution is approximately 0.1 mg/mL. For example, if the drug product label claim is 250 mg/mL, weigh approximately 100 mg of sample into a weigh pan and transfer to a 250-mL volumetric flask. Quantity sufficient (QS) with HPLC or deionized water.

In solution formation, no drug product should remain undissolved on the pan.

Lyophilized Formulations

Techniques for making lyophilized formulations are illustrated in the following paragraphs. One skilled in the art is capable of altering these procedures in the practice of the invention.

Using a disposable syringe, a drug-product vial can be filled approximately three-quarters full with HPLC or deionized water. A vortex can be used to dissolve the sample. Without removing the septum, a syringe can be used to transfer quantitatively the contents of the vial to a suitable volumetric flask. The vial should be rinsed at least five times with deionized water and the rinses added to the volumetric flask. Next, the volume can be diluted with deionized water. If necessary, use "to contain" pipettes and volumetric flasks to dilute this solution further to produce a 0.1±0.01 mg per mL solution for analysis. It is desirable to prepare a duplicate sample in an identical fashion.

Sample preparation procedures for other formulations can be developed as required. Such procedures are within the skill level of one skilled in the art.

7. Procedure

The practice of the invention is illustrated by the following procedures. One skilled in the art is capable of altering these procedures as needed.

It is desirable to use dedicated glassware to prepare mobile phases for IP-HPLC-MS. Solutions can be scaled up or down as appropriate.

Preparation of Mobile Phases 100 mM TBuAA (Tributylammonium Acetate) Stock Solution Under a blanket of argon, add approximately 450 mL of acetonitrile to a 500-mL graduated cylinder. Using disposable pipettes add 12 mL of tributylamine from an unopened bottle and 3 mL of glacial acetic acid. QS to a final volume of 500 mL with acetonitrile. Transfer to a 1-L amber-colored bottle, stir at room temperature until completely mixed. Store under a layer of argon gas at room temperature. When stored at room temperature the stock solution has a shelf life of 2 months.

Alternatively, stock solution may be prepared replacing acetonitrile with bottled HPLC water. However, solutions prepared in this manner will require stirring for at least three hours to ensure complete mixing. The mobile phase preparations should be adjusted accordingly.

100 mM EDTA (Ethylenediaminetetraacetic Acid) Stock Solution

Transfer 7.3 g of EDTA, 12 mL of tributylamine and approximately 200 mL of bottled HPLC water to a 250-mL volumetric flask. Stir until all the EDTA is dissolved, and then dilute to a final volume of 250 mL with bottled HPLC water. Store under a layer of argon gas at room temperature. When stored at room temperature the stock solution has a shelf life of 6 months.

Mobile Phase A. (5 mM TBuAA, 10% Acetonitrile, 1 uM EDTA)

Under a blanket of argon, use a disposable pipette to transfer 50 mL of 100 mM TBuAA stock solution to a 1-L graduated cylinder. Add 50 mL of ACN and 10 uL of 100 nM EDTA stock solution. QS to 1000 mL with bottled HPLC water. Transfer to an amber-colored HPLC bottle and layer with argon gas. Mix well. When stored at room temperature the solution has a shelf life of 2 months.

In some embodiments, the volume of acetonitrile can be increased from 50 mL to 100 mL if aqueous stock solution is used.

Mobile Phase B. (5 mM TBuAA, 80% Acetonitrile, 1 uM EDTA)

Under a blanket of argon, use a disposable pipette to transfer 50 mL of 100 mM TBuAA stock solution to a 1-L graduated cylinder. Add 750 mL of ACN and 10 uL of 100 mM EDTA stock solution. QS to 1000 mL with bottled HPLC water. Transfer to an amber-colored HPLC bottle and layer with argon gas. Mix well. When stored at room temperature the solution typically has a shelf life of about 2 months.

In some embodiments, the volume of acetonitrile is increased from 750 mL to 800 mL if aqueous stock solution is used.

Suggested injection sequences are shown in the table below.

| Sample | Injection volume (uL) | Number of injections |
|---|---|---|
| Blank | 25 | 2 |
| Reference standard | 10 | 1 |
| Reference standard | 20 | 1 |
| Reference standard | 25 | 1 |
| Reference standard | 30 | 1 |

-continued

| Sample | Injection volume (uL) | Number of injections |
|---|---|---|
| Check reference standard (if applicable) | 25 | 1 |
| Reference standard | 25 | 1 |
| Sample A, preparation 1 | 25 | 1 |
| Sample A, preparation 2 | 25 | 1 |
| Reference standard | 25 | 1 |
| Blank | 25 | 1 |

Multiple samples may be injected between adjacent 25-uL reference standard injections but the results are reportable only for those samples between adjacent injections that meet the system suitability requirements in 4.1, 4.2, 4.3 and 4.4. In any single run, a maximum of 30 injections (including additional 25-uL reference standard and blank injections) can be typically made before the calibration curve needs to be repeated.

At the end of the sequence, the column can be rinsed with a 1:1 solution of acetonitrile in water (bottled HPLC grade) for 15 min at a flow rate of 0.2 mL per minute.

Data Analysis

Data analysis is illustrated by the following non-limiting examples.

System suitability requirement in 4.1 should be met. The UV trace of the 10, 20, 30 and the first 25-uL injection of the reference standard should be analyzed. The water blank is subtracted from each trace and the area of the main UV peak (y-variable) is plotted against the amount (in ug) of IN-pure standard on column (x-variable). The amount of UV-pure standard on column can be calculated by multiplying the total oligonucleotide concentration of the standard by its UV purity and the injection volume. The correlation coefficient ($R^2$) can be obtained from linear regression analysis and reviewed to ensure that the system suitability requirement in 4.5 is met.

The EICs should be integrated due to the appropriate charge state of the main component and its major impurity for the 10, 20, 30 and the first 25-uL injection of the reference standard. For each injection, the ion current areas for the two components are added together and a second-order polynomial analysis of the summed area against injection volume is performed. The graph should be forced through zero. The relationship between EIC and injection volume can be reported in the form $y=Ax^2+Bx$ and the correlation coefficient $R^2$. One should ensure that the system suitability requirement in 4.6 is met.

The UV trace of the remaining 25-uL injections of the reference standard bracketing the samples can be analyzed. The water blank is subtracted from each trace and the relative standard deviation (RSD) of the area of the main peak for the three 25-uL injections is calculated. The average UV purity for the three 25-uL injections of the reference standard can be reported. One should ensure the system suitability requirements in 4.2 and 4.3 are met.

The mass of the main component of the main UV peak of the three 25-uL injections of the reference standard bracketing the samples can be reported. One should ensure the system suitability requirement in 4.4 is met.

If using drug substance as the reference standard, the response factor (Rf) can be calculated for the first 25-uL injection of the reference standard and the reference standard injection checked using the following equation:

$$Rf = \frac{AreaCountofMainPeak}{TotalOligoConcentration}$$

$$\% \text{ Agreement} = \frac{Rf_{reference} - Rf_{checkstandard}}{Rf_{reference}} \times 100\%$$

One should ensure the system suitability requirement in 4.7 is met.

The UV trace of the first preparation of each sample can be analyzed and the blank subtracted. The UV-peak areas can be reported and grouped as follows:

| Species | Criterion* |
|---|---|
| Early eluting peaks | RRT < 0.98 |
| Late eluting peaks | RRT > 1.05 |

*Relative retention times are approximate values only

The UV area-% for all peaks can be reported and calculations performed as described in Calculations section below.

The UV trace of the second sample preparation can be analyzed. For both preparations of each sample, the least squares line, as calculated above, is used to calculate the amount of UV-pure material (in ug) on column. The concentration of UV-pure material in each sample preparation (in ug/uL) is determined by dividing by the injection volume.

The drug substance and drug product samples, for example, can be analyzed by the ion-pair liquid chromatography mass-spectrometry (IP-LC-MS) method to determine impurity profile and assay or label claim as appropriate. To assess the suitability of the method for this purpose, experiments aimed at evaluating method accuracy, linearity, range, repeatability, intermediate precision and the limits of detection and quantitation were devised.

The least squares analysis can be calculated as shown below.

$$\bar{x} = \sum x_i / N$$

$$\bar{y} = \sum y_i / N$$

$$S_{xx} = \sum (x_i - \bar{x})^2 = \sum x_i^2 - \left(\sum x_i\right)^2 / N$$

$$S_{yy} = \sum (y_i - \bar{y})^2 = \sum y_i^2 - \left(\sum y_i\right)^2 / N$$

$$S_{xy} = \sum (x_i - \bar{x})(y_i - \bar{y}) = \sum x_i y_i - \sum x_i \sum y_i / N$$

$$m = S_{xy} / S_{xx} \text{ (Slope)}$$

$$b = \bar{y} - \bar{x} m \text{ (Y-intercept)}$$

$$s_r = \sqrt{\frac{S_{yy} - m^2 S_{xx}}{N - 2}}$$

$$s_m = \sqrt{s_r^2 / S_{xx}}$$

$$s_b = s_r \sqrt{\frac{1}{N - (\sum x_i)^2 / \sum x_i^2}}$$

$s_r$=standard deviation of the regression
$s_m$=standard deviation of the slope
$s_b$=standard deviation of the intercept
$\bar{x}$=mean value of x for the sample.
$\bar{y}$=mean value of y determined for the sample
N=number of points in calibration curve.

Precision:

$$\text{Standard deviation } (sd) \text{ between samples} = \sqrt{\frac{1}{c-1} \sum (\bar{X}_i - \bar{\bar{X}})^2}$$

$$sd \text{ within samples} = \sqrt{\frac{\sum (X_{1i} - \bar{X}_1)^2 + (X_{2i} - \bar{X}_2)^2 + (X_{3i} - \bar{X}_3)^2 \ldots}{c(n-1)}}$$

$\bar{X}_i$=mean of sample i
$\bar{\bar{X}}$=grand mean
$X_{1t}$=value of the $t^{th}$ observation of sample 1
$\bar{X}_1$=mean of sample 1
c=number of samples
n=number of observations of each sample The co-eluting species in the main UV peak of the first sample preparation are accounted for by analyzing the total ion current (TIC) detected by the mass spectrometer. The average mass spectrum is smoothed to a Gaussian width of 0.5 amu. One then extracts and integrates the appropriate charge state of all species listed in Table 1 below. Also, one extracts and integrates the same charge state of any additional components listed in the relevant material specification.

In practice, it is desirable to examine the average mass spectrum of each sample for new impurities.

For mass to charge ratios (m/z) of less than that of the major impurity, one can extract and integrate the same charge state of any additional components that have peaks heights of ≧0.20% that of the main peak.

For m/z of greater than CNET impurity, one can extract and integrate the appropriate charge state of any additional components that have peak heights of ≧0.40% that of the main peak.

In both cases, it is preferred to only extract additional components that are well resolved from any specified impurity. To judge whether an additional component is sufficiently resolved to warrant extraction, one can measure the relative peak height of the smaller of the two components and the height of the valley between the two components. Typically one only extracts and integrates the additional component if the relative peak height to valley height ratio is ≧2.0. If two additional components are not well resolved from each other, one can extract and integrate the larger component only.

The presence of sodium and potassium adducts make it impossible to extract and integrate components with masses slightly larger than that of the parent compound. For this reason, one typically would not attempt to extract and integrate any components with m/z between that of the parent compound and the CNET impurity.

In some embodiments, calculations are performed as described in Calculations section below.

TABLE 1

List of components to be extracted

| Name of Species | Abbreviation |
|---|---|
| Full length, target oligonucleotide | n |
| Monophosphate diester | (P=O)$_1$ |
| Diphosphate diester | (P=O)$_2$ |
| n − 1 species, n − p(dA) | n − p(dA) |

TABLE 1-continued

List of components to be extracted

| Name of Species | Abbreviation |
|---|---|
| n − 1 species, n − p(dC) | n − p(dC) |
| n − 1 species, n − p(dG) | n − p(dG) |
| n − 1 species, n − pT and/or n − p(methyl-C) | n − pT, n − p($^{Me}$C) |
| n − 1 species, n − p(MOE A)[#] | n − p(MOE A) |
| n − 1 species, n − p(MOE methyl-C) and/or n − p(MOE methyl-U)[#] | n − p(MOE $^{Me}$C) n − p(MOE $^{Me}$U) |
| n − 1 species, n − p(MOE G)[#] | n − p(MOE G) |
| 3'-Terminal phosphorothioate monoester | 3'-TPT |
| Depurination species, loss of guanine | -Gua |
| Depurination species, loss of adenine, or loss of guanine with water added | -Ade and/or -Gua + H$_2$0 |
| Depurination species, loss of adenine with water added and/or loss of guanine with methanol added | -Ade + H$_2$0 and/or -Gua + MeOH |
| Depurination species, loss of adenine with methanol added | -Ade + MeOH |
| 2'-O-methyl species[#] | 2'-OCH$_3$ |
| Ethylenephosphorothioate diester species | EPD |
| Trichloroethanol-modified species | TCE |
| 3-(2-Cyanoethyl)thymidine-modified species | CNET |
| n + 1 species, n + p(dA)** | n + p(dA) |
| n + 1 species, n + p(dC)** | n + p(dC) |
| n + 1 species, n + p(dG)** | n + p(dG) |
| n + 1 species, n + pT and/or n + p(d methyl-C)** | n + pT, n + p(d$^{Me}$C) |
| "+97 amu" impurity*, ** | +97 amu |

*Approximate observed mass values, extract and integrate the observed signal due to the appropriate charge state
**Impurity masses are confounded with adduct masses, integrate only the appropriate region of the extracted ion chromatogram.
[#]MOE sequences only The list given in Table 1 is subject to sequence considerations. For example, if the particular sequence does not contain any MOE G residues then the ion corresponding to n-p (MOE G) would not be extracted.

8. Calculations

Drug Substance and Drug Product Impurity Profile

Impurities Outside the Main UV Peak

For each impurity detected outside of the main UV peak of the first preparation of each sample, the UV area percent of that peak can be determined according to the following equation:

$$IMP_o^i = \frac{UV_{area}^i}{\sum_i UV_{area}^i} \times 100\%$$

where
$IMP_o^i$=percent contribution to the sample of component i outside of the main UV peak;
$UV_{area}^i$=UV area of component i outside of the main UV peak; and $$\sum_i UV_{area}^i =$$

sum of the UV areas of all peaks.

Components Inside the Main UV Peak

A calibration curve can be established by the 10, 20, 25 and 30-uL injections of the reference standard. The second-order polynomial equation is used to calculate a combined effective volume of injection for the full-length, target oligonucleotide and its major impurity and individual effective volumes of injection for all other species contained within the main UV peak. These effective volumes of injection can be used to determine the amount of each component present. However, because the two quantities are directly proportional, the effective volumes of injection can be used without transformation to determine the relative percentages.

The area of the integrated ion-current due to component i ($IC_i$) is given by the second-order polynomial $$IC_i = A \times V_i^2 + B \times V_i$$

where A and B are the factors determined from the standard curve and $V_i$ is the effective volume of injection of component i. Note that for the full-length oligonucleotide and its major impurity, $IC_i$ is the sum of the ion currents due to both species and $V_i$ is their summed effective volume of injection. This equation is solved for $V_i$ for each component extracted from within the main UV peak. The individual effective volumes of injection of the full-length, target oligonucleotide ($V_n$) and its major impurity ($V_{P=O}$) are calculated from their summed effective volume of injection ($V_{n+P=O}$) as follows:

$$V_n = V_{n+P=O} \times \frac{IC_n}{IC_n + IC_{P=O}}$$

and $$V_{P=O} = V_{n+P=O} \times \frac{IC_{P=O}}{IC_n + IC_{P=O}}$$

where $IC_n$ and $IC_{P=O}$ are the ion currents due to the full-length, oligonucleotide and its major impurity, respectively. The relative amounts of component i contained within the main UV peak expressed as decimal fraction is given by:

$$\text{component } i = \frac{V_i}{\sum_i V_i}$$

The amount of component i expressed as a percentage of the total sample is calculated by multiplying the relative amount of component i expressed as a decimal fraction of the main UV peak by the UV purity of the sample (calculated by dividing the UV area of the main UV peak by the total UV area) as follows:

$$IMP_w^i = \frac{V_i}{\sum_i V_i} \times \frac{UV_{area}^m}{\sum_i UV_{area}^i} \times 100\%$$

where
$IMP_w^i$=the percent contribution to the sample of component i within the main UV peak; and
$UV_{area}^m$=area of the main UV peak.

For the first preparation of each sample the percent contribution of each species (including the full-length oligonucleotide,) extracted from within the main UV peak can be calculated according to the equations described above.

In some embodiments, the limit of detection (LOD) for the $(P=O)_1$ component is 0.25%, the LOD for all other components is 0.10%. The area percents of all those components i that are present at or above the LOD can be summed.

The percent contribution to the sample of those components present at or above the LOD can be calculated by multiplying their area percent (described above) by the total area percent calculated for the component divided by the total area percent calculated for all components.

Values can be reported as follows.

Impurity Categories Composed of Single Components, e.g., TCE, CNET

Representative impurity categories are presented in the following paragraphs.

The limit of quantitation (LOQ) for the $(P=O)_1$ component is typically 0.40%, the LOQ for all other components is typically 0.20%.

If the measured value is at or above the LOQ and below 1.0%, the measured value can be rounded to two decimal places. If the measured value is at or above 1.0%, the measured value can be rounded to one decimal place.

If the measured value is at or above the LOD but below LOQ, a value of <LOQ followed by the measured value in parentheses rounded to two decimal places typically should be reported.

If the measured value is below the LOD, "ND" (not detected) followed by the LOD value in parentheses rounded to two decimal places can be reported.

Some preferred reporting procedures are illustrated by example in the following tables.

Situation 1. Impurity Categories Composed of Single Components

| Component | Measured value (%) | Reported value (%) |
|---|---|---|
| $(P=O)_1$ | 2.1345 | 2.1 |
| CNET | 0.5162 | 0.52 |
| TCE | 0.1637 | <LOQ (0.16) |
| $(P=O)_2$ | 0.0893 | ND (<0.10%) |

Impurity Categories Composed of Multiple Components, e.g., Total n−1, Total Depurination Those components that are present above the LOD are summed.

If two or more components are summed, the total should be reported. If the total is below 1.0%, the total is typically rounded to two decimal places. If the total is at or above 1.0%, the total is typically rounded to one decimal place.

If a single component is present at or above the LOQ, the value is reported. If the value is below 1.0%, the value can be rounded to two decimal places. If the value is at or above 1.0%, the value can be rounded to one decimal place.

If only one component is present at or above the LOD and below the LOQ, the value can be reported as <LOQ followed by the measured value in parentheses rounded to two decimal places.

If all the components are present below the LOD, the total is reported as not detected (ND) followed by the LOD value in parentheses rounded to two decimal places.

Some preferred reporting procedure is illustrated by example in the following tables.

Situation 2: Two or More Components are Present at or Above the LOD

| Component | Measured individual value | Reported total value |
|---|---|---|
| -Gua | 0.0980 | 0.66 |
| -Ade and/or -Gua + $H_2O$ | 0.1876 | |
| -Ade + $H_2O$ and/or -Gua + MeOH | 0.3156 | |
| -Ade + MeOH | 0.1632 | |

Situation 3: A Single Component is Present at or Above the LOQ

| Component | Measured individual value | Reported total value |
|---|---|---|
| -Gua | 0.0983 | 0.32 |
| -Ade and/or -Gua + $H_2O$ | 0.0945 | |
| -Ade + $H_2O$ and/or -Gua + MeOH | 0.3179 | |
| -Ade + MeOH | 0.0876 | |

Situation 4: A Single Component is Present at or Above the LOD and Below the LOQ

| Component | Measured individual value | Reported total value |
|---|---|---|
| -Gua | 0.0983 | <LOQ (0.18) |
| -Ade and/or -Gua + $H_2O$ | 0.0945 | |
| -Ade + $H_2O$ and/or -Gua + MeOH | 0.1785 | |
| -Ade + MeOH | 0.0876 | |

Situation 5: All Components are Present Below the LOD

| Component | Measured individual value | Reported total value |
|---|---|---|
| -Gua | 0.0056 | ND (<0.10%) |
| -Ade and/or -Gua + $H_2O$ | 0.0965 | |
| -Ade + $H_2O$ and/or -Gua + MeOH | 0.0987 | |
| -Ade + MeOH | 0.0896 | |

Drug Substance Assay

The percent purity of the drug substance on an anhydrous, solvent and salt free basis can be determined for each sample preparation as follows:

$$\% \text{ Purity} = \frac{V_{sample} \times C_{sample} \times MSP_{sample}}{W_{sample} \times (1.0000 - S)} \times 100$$

where $V_{sample}$=volume (mL) of each sample preparation (e.g., 250 mL);

$C_{sample}$=concentration of UV-pure material in each sample preparation in ug/uL;

$\text{MSP}_{sample}$=mass spectrometric purity of the main UV peak of the sample expressed as a decimal fraction. The MSP is calculated by dividing the sum of the percent contributions to the sample of the full length, target oligonucleotide and its major impurity by the UV purity of the sample. The UV purity is determined on the first preparation of each sample and is defined as the decimal fraction of the peak area of the main UV peak divided by the total UV area;

$\text{W}_{sample}$=weight of each sample preparation (mg); and

S=decimal fraction of sum of water, solvents and sodium acetate.

An average assay value can be calculated for each sample. In calculating the value, the number can be rounded and reported to one decimal place in some embodiments.

Drug Substance Mass Balance

The agreement between the assay and impurity profile values for the drug substance can be determined by subtracting the sum of the full-length oligonucleotide and major impurity material from the average assay value. It is desirable that the two values agree to within an absolute value of ±4.0%.

Drug Product Label Claim

In some embodiments, the method can be used to support a drug product label claim. The % label claim of each drug product preparation can be determined as follows:

$$\% \text{ Label Claim} = \frac{C_{sample} \times MSP_{sample} \times DF}{LC_{sample}} \times 100$$

where $C_{sample}$=concentration of UV-pure material in each sample preparation in ug/uL;

$\text{MSP}_{sample}$=mass spectrometric purity of the main UV peak of the sample expressed as a decimal fraction. The MSP is calculated by dividing the sum of the percent contributions to the sample of the full length, target oligonucleotide and its major impurity by the UV purity of the sample. The UV purity is determined on the first preparation of each sample and is defined as the decimal fraction of the peak area of the main UV peak divided by the total UV area;

DF=Dilution Factor (see note); and $LC_{sample}$=label claim.

It should be noted that to calculate the correct dilution factor for viscous solutions, the weight of the sample transferred must be converted into a volume by dividing by the density of the drug product solution. The density of any given lot is typically available from the batch production record.

For some drug product formulations, e.g., lypohiles, dilution factor is replaced by final sample volume.

In some embodiments, the value is reported as the average % label claim to one decimal place.

EXAMPLES

By way of illustration, the analysis of a sample of 20 nucleotide 5-10-5 2'-O-methoxyethyl gapmer is presented below.

Example 1

Evaluation of Test Methods

System Suitability

To confirm proper functioning of the instrument, system suitability injections were run prior to and upon completion of each experiment. The results from these injections were assessed against the acceptance criteria.

Linearity and Range of the Main Component

We assessed the linearity of the UV response by injecting various amounts of 20 nucleotide 5-10-5 2'-O-methoxyethyl gapmer. The main UV peak from each injection was integrated and plotted a graph of UV response against column load. The results are shown in FIG. 2.

The results indicated that the response was linear and the intercept negligible over a range of sample loads from approximately 0.005 ug to 7.5 ug. This range encompasses approximately 0.2% to 300% of the targeted column load of 2.5 ug.

The linearity of the mass spectral response for the same set of samples was assessed. For each sample we extracted and integrated the ion currents due to the full-length, fully thioated and full-length, monophosphate diester components. The summed ion currents were plotted against amount of sample on column. The results of this experiment are shown in FIG. 3.

As expected from our prior work with oligonucleotides, the response was not linear and flattened off at higher sample loads. This effect is believed to be due to ion suppression. In essence, at high oligonucleotide concentrations there is insufficient space on a single droplet to accommodate in a linear fashion more and more molecules for ionization. With the exception of the monophosphate diester component, all process related and degradation products within the main UV peak identified to date resolve chromatographically to some degree from the main component. Because they resolve from the main component and because they are present at low levels, such impurities suffer much less ion suppression than the main component and its non-resolving monophosphate diester impurity. As a consequence, levels of these components are overestimated if one simply compares their integrated ion currents to that of the parent component. To correct for this effect, a 4-point calibration curve, generated by injecting various volumes of a standard solution of 20 nucleotide 5-10-5 2'-O-methoxyethyl gapmer, is prepared. The ion currents due to the full-length, fully-thioated component and its monophosphate diester are extracted and integrated. The summed ion currents for each injection are plotted against injection volume and the resulting points fit by a second order polynomial equation. The graph is forced through zero. The resulting quadratic equation is used to interpret the integrated ion currents due to individual impurities and to the combined ion current due to the full-length, fully-thioated component and its monophosphate diester in the sample. These values, euphemistically termed "effective volumes of injection", are compared to each other to determine the mass spectral impurity profile. To check the validity of this approach, we fit a quadratic equation to the data shown in FIG. 3 using the responses corresponding to the 4-point calibration curve. The graph was forced through zero in the normal fashion. Inspection of FIG. 3 confirmed that the measured response was described accurately by the calibration curve at column loads of less than or equal to approximately 2.5 ug. The measured values at higher column loads (data not plotted) were significantly higher than those predicted by extrapolation of the quadratic curve. As the ion current due to any single species in a sample is always less than the ion current due to the sum of the full length, fully-thioated component and its monophosphate diester, this result is of little practical consequence.

The results in this section demonstrated that the UV response was linear ($R^2=1.0000$) with negligible intercept over the range of column loads investigated. The results also confirmed the non-linearity of the mass spectral response and the validity of the quadratic curve algorithm detailed as a means of dealing with this curvature.

Accuracy, Linearity and Range of Authentic Impurities

Accuracy (recovery), linearity and range for impurities were assessed by analysis of solutions of 20 nucleotide 5-10-5 2'-O-methoxyethyl gapmer spiked with known amounts of phosphate diester impurity 1 and n-p(MOE methyl U) impurity 2 (Scheme 1).

Scheme 1.
Structures of 20 nucleotide 5-10-5 2'-O-methoxyethyl gapmer and authentic impurities

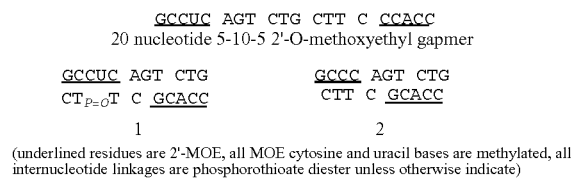

(underlined residues are 2'-MOE, all MOE cytosine and uracil bases are methylated, all internucleotide linkages are phosphorothioate diester unless otherwise indicate)

Stock solutions of 20 nucleotide 5-10-5 2'-O-methoxyethyl gapmer and the two impurities were prepared by dissolving lyophilized material in water. The total oligonucleotide concentrations of the stock solutions were determined by UV spectroscopy against a standard solution of known concentration. The total oligonucleotide concentrations were multiplied by the sample purities as determined by IP-LC-MS to give estimates of the main component concentrations. These stock solutions were then used to prepare samples of 20 nucleotide 5-10-5 2'-O-methoxyethyl gapmer spiked with various amounts of each impurity. The samples were then analyzed. For each injection only those ion currents due to the full-length, fully-thioated component, 1 and 2 if appropriate, were extracted and integrated. The results of these experiments are given in Tables 2 and 3.

TABLE 2

Spiked and Recovered Levels of Impurity 1.

| % Spiked | Injection | % Measured |
|---|---|---|
| 0 | 1 | 2.70 |
|   | 2 | 2.70 |
|   | 3 | 2.74 |
|   | 4 | 2.53 |
|   | 5 | 2.64 |
| 0.82 | 1 | 3.07 |
|   | 2 | 3.22 |
|   | 3 | 2.97 |
| 3.39 | 1 | 5.35 |
|   | 2 | 5.58 |
| 7.08 | 1 | 9.06 |
|   | 2 | 8.78 |
| 11.10 | 1 | 12.20 |
|   | 2 | 12.79 |
|   | 3 | 12.42 |

TABLE 3

Spiked and Recovered Levels of Impurity 2.

| % Spiked | Injection | % Measured |
|---|---|---|
| 0 | 1 | 0.41 |
|   | 2 | 0.40 |
|   | 3 | 0.44 |
|   | 4 | 0.43 |
|   | 5 | 0.35 |
| 0.41 | 1 | 0.79 |
|   | 2 | 0.84 |
|   | 3 | 0.82 |
| 0.83 | 1 | 1.34 |
|   | 2 | 1.25 |
| 1.26 | 1 | 1.86 |
|   | 2 | 1.87 |
| 1.68 | 1 | 2.31 |
|   | 2 | 2.02 |
| 2.55 | 1 | 3.18 |
|   | 2 | 3.30 |
|   | 3 | 3.08 |

The data in Tables 2 and 3 were used to make graphs of amount spiked against amount recovered. The resulting plots are shown in FIGS. 4 and 5, respectively.

The data in FIG. 4 indicates that recovery for impurity 1 was 89% over a range of approximately 2 to 12% w/w. The response was linear ($R^2=1.00$) over the same range. The y-intercept of the regression line was a good approximation of the native level. For impurity 2, the average recovery over a range of approximately 0 to 3% w/w was ca. 109%. The response was linear ($R^2=0.99$) over the same range. The y-intercept of the regression line was a good approximation of the native level.

The results in this section demonstrated recoveries for authentic impurities 1 and 2 were excellent over the range of levels examined. The method demonstrated good linearity for both authentics ($R^2>0.99$) over the range of concentrations examined. In addition, the y-intercepts of plots of spiked against measured authentic content were excellent estimations of native levels.

The demonstrated accuracy and linearity with negligible y-intercept mean that reporting area percent is an accurate estimation of weight percent.

Precision

Drug Substance. Repeatability within and between sample preparations and between analysts was assessed by three analysts. Analyst 1 prepared three samples of drug substance. Each sample was analyzed in triplicate. Analysts 2 and 3 each prepared two samples of the same drug substance and analyzed each sample in duplicate. Each analyst used a different instrument, column and set of mobile phases. To ensure identical water contents between sample preparations, the analysts weighed out samples of equilibrated drug substance at the same time. This allowed a comparison of relative assay values between samples and analysts without the need for multiple, separate water content analyses.

The average impurity profiles and assay value results (assuming a water content of 18%) determined by each analyst are given in Tables 4 and 5. Impurities were grouped and reported as per the proposed drug substance material specifications. Within and between sample percent relative standard deviations (% RSD) were calculated according to the formulae given above.

TABLE 4

Analyst 1 Within and Between Sample Variability For Drug Substance

| Component | Mean | % RSD Between Samples | % RSD Within Samples |
|---|---|---|---|
| 20 nucleotide 5-10-5 2'-O-methoxyethyl gapmer | 92.50 | 0.11 | 0.32 |
| Full Length (n) | 90.72 | 0.15 | 0.31 |
| (P=O)$_1$ | 1.79 | 1.67 | 5.00 |
| (P=O)$_2$ | 0.12 | 7.21 | 9.02 |
| Total n − 1 | 0.85 | 8.19 | 10.82 |
| Total n + 1 | 0.17 | 13.15 | 25.97 |
| Total depurination | 0.33 | 6.62 | 14.36 |
| Total TPT | ND | NA | NA |
| CNET | 0.13 | 5.27 | 0.00 |
| TCE | ND | NA | NA |
| EPD | 0.12 | 7.21 | 0.00 |
| 2'-OCH$_3$ | 0.34 | 1.13 | 0.96 |
| n-108 amu | 0.16 | 4.40 | 24.52 |
| n-58 amu | 0.12 | NA | NA |
| Any single other impurity | 0.44 | 2.96 | 6.88 |
| Total other impurities | 0.44 | 2.96 | 6.88 |
| Early eluting impurities | 1.21 | 2.00 | 4.25 |
| Late eluting impurities | 3.89 | 0.47 | 0.66 |
| Assay | 92.28 | 0.21 | 0.23 |

The results presented in Table 4 demonstrated excellent within and between sample precision in the 20 nucleotide 5-10-5 2'-O-methoxyethyl gapmer, full-length, fully-thioated component and assay categories. For the drug substance, the % RSDs within and between samples for 20 nucleotide 5-10-5 2'-O-methoxyethyl gapmer content, full-length, fully-thioated content and assay were 0.32, 0.11, 0.31, 0.15, 0.23, and 0.21, respectively Within and between sample % RSDs for the impurities, although higher, were acceptable given their lower concentrations. Excluding those impurities present below 0.2% (the approximate method LOQ, vide infra), between sample and within sample % RSDs ranged from 0.47 to 8.19 and 0.66 to 14.36, respectively. The average between samples and within sample % RSDs were 3.98 and 7.45.

Variability between analysts was estimated by comparing the average impurity profiles and assay values determined by each analyst. The results of this analysis are given in Table 5.

TABLE 5

Variation Between Analysts For Drug Substance

| Component | Mean Analyst 1 | Mean Analyst 2 | Mean Analyst 3 | % RSD between Analysts | Range of observed values* |
|---|---|---|---|---|---|
| 20 nucleotide 5-10-5 2'-O-methoxyethyl gapmer | 92.50 | 91.97 | 91.98 | 0.33 | 91.89-92.79 |
| Full Length (n) | 90.72 | 90.40 | 90.21 | 0.28 | 90.06-91.05 |
| (P=O)$_1$ | 1.79 | 1.57 | 1.77 | 7.23 | 1.42-1.92 |
| (P=O)$_2$ | 0.12 | ND | ND | NA | 0.10-0.14 |
| Total n − 1 | 0.85 | 0.68 | 0.76 | 10.72 | 0.64-0.99 |
| Total n + 1 | 0.17 | 0.11 | 0.11 | 27.91 | 0.11-0.23 |
| Total depurination | 0.33 | 0.43 | 0.48 | 18.66 | 0.28-0.48 |
| Total TPT | ND | ND | ND | NA | NA |
| CNET | 0.13 | 0.20 | 0.22 | 27.69 | 0.12-0.25 |
| TCE | ND | ND | ND | NA | NA |
| EPD | 0.12 | ND | 0.10 | 9.71 | 0.10-0.13 |
| 2'-OCH$_3$ | 0.34 | 0.34 | 0.33 | 1.23 | 0.29-0.37 |
| n-108 amu | 0.16 | 0.15 | 0.17 | 7.36 | 0.10-0.20 |
| n-58 amu | 0.12 | ND | ND | NA | 0.12 |

TABLE 5-continued

Variation Between Analysts For Drug Substance

| Component | Mean Analyst 1 | Mean Analyst 2 | Mean Analyst 3 | % RSD between Analysts | Range of observed values* |
|---|---|---|---|---|---|
| Any single other impurity | 0.44 | 0.50 | 0.55 | 11.82 | 0.39-0.58 |
| Total other impurities | 0.44 | 0.50 | 0.55 | 11.82 | 0.39-0.58 |
| Early eluting impurities | 1.21 | 0.87 | 1.30 | 20.44 | 0.86-1.32 |
| Late eluting impurities | 3.89 | 4.82 | 3.93 | 12.44 | 3.86-4.86 |
| Assay | 92.28 | 92.39 | 91.10 | 0.78 | 90.89-92.69 |

*Ranges are the lowest and highest values obtained by different analysts.

In general, there was good agreement between the average values obtained by the different analysts. In the majority of cases, % RSDs between analysts were less than 15 for the impurity categories and less than 1 for assay, 20 nucleotide 5-10-5 2'-O-methoxyethyl gapmer and full-length, fully thioated content of the drug substance. A notable exception was the early and late eluting impurity category where the observed % RSDs were 20.44 and 12.44, respectively. The higher % RSDs are believed to be due to a larger than expected differences between the average values determined by Analyst 2 and those determined by the other two analysts.

Drug Product. 20 Nucleotide 5-10-5 2'-O-methoxyethyl gapmer drug product is a solution of drug substance in water for injection (WFI). As no excipients are added during the manufacturing process, we felt the data gathered in the drug substance section was sufficient to demonstrate repeatability and precision for drug product analyses and designed additional experiments to assess only the sample preparation portion of the analysis. The experiments and the results obtained are described below.

The repeatability of the drug product sample preparation procedure was assessed by three analysts. To prepare each sample, approximately 100 mg of drug product was weighed onto a foil weighing pan or weighing boat then quantitatively transferred into a 250-mL volumetric flask. The volumetric flask was filled to volume with de-ionized water and mixed well. Analyst 1 prepared five samples and Analysts 2 and 3 an additional two each. Analyst 1 then analyzed the UV trace of all samples. The normalized UV areas (ratio of the UV area of the main peak to the sample weight) of each sample were compared. The results are presented in Table 6.

TABLE 6

Variation Between Analysts Sample Preparations For Drug Product

| Analyst | Sample | UV area | Sample weight (mg) | Normalized UV area | Mean Normalized UV area | % RSD within analyst | % RSD between analysts |
|---|---|---|---|---|---|---|---|
| 1 | 1 | 7787.30 | 111.80 | 69.65 | 69.75 | 0.46 | 0.35 |
|   | 2 | 7744.27 | 110.80 | 69.89 |   |   |   |
|   | 3 | 7679.94 | 110.92 | 69.24 |   |   |   |
|   | 4 | 7784.89 | 111.08 | 70.08 |   |   |   |
|   | 5 | 7767.38 | 111.16 | 69.88 |   |   |   |
| 2 | 1 | 7488.07 | 107.27 | 69.81 | 70.07 | NA |   |
|   | 2 | 7551.16 | 107.36 | 70.33 |   |   |   |
| 3 | 1 | 7302.66 | 104.56 | 69.84 | 69.57 | NA |   |
|   | 2 | 7515.84 | 108.47 | 69.29 |   |   |   |

The data presented in Table 6 show that the sample preparation portion of drug product analysis demonstrates excellent within and between analyst precision. The % RSDs within and between analysts were 0.46 and 0.35, respectively. When combined with the drug substance data above, these results demonstrate the method is sufficiently precise for the analysis of 20 nucleotide 5-10-5 2'-O-methoxyethyl gapmer drug product.

Limits of Detection (LOD) and Quantitation (LOQ)

The data obtained in the impurity recovery section was used to calculate LOD and LOQ values for authentics 1 and 2 according the following equations:

$$LOD = \frac{3s}{m} \text{ and } LOQ = \frac{5s}{m}$$

where m and s are equal to the slope and standard deviation of the y-intercept, respectively, obtained by plotting % measured against % spiked for each impurity.

The slopes, standard deviations of the y-intercepts and the calculated LOD and LOQ values for impurities 1 and 2, as percentages of the full-length fully-thioated component, in these solutions sample are given in Table 7.

TABLE 7

LOD and LOQ For Authentics 1 and 2

| Authentic | Slope, m | Standard deviation of y-intercept | LOD (% of n) | LOQ (% of n) |
|---|---|---|---|---|
| 1 | 0.89 | 0.07 | 0.23 | 0.38 |
| 2 | 1.09 | 0.03 | 0.08 | 0.14 |

The results in this section indicate the method is sensitive enough to detect and quantitate low-level impurities in the presence of the sample matrix.

Specificity

We did not address the issue of method specificity directly during this study. However, the described method employs simultaneous chromatographic and mass spectral separation techniques, the combination of which is expected to be specific. The stability indicating nature of the method has been confirmed through stress studies.

Example 2

Analysis of a 20 Nucleotide 5-10-5 2'MOE Gapmer Phospohorothioate Drug Substance by Ion-Pair HPLC with UV and Mass Spectrometry Detection Sample and Standard Preparation 29.83 mg and 29.69 mg of the drug substance were transferred to separate 250-mL volumetric flasks and the flasks made to volume with purified water. An aliquot of each solution was transferred to an HPLC vial. A standard solution of the drug substance at a UV pure oligonucleotide concentration of 0.099 mg/mL was transferred to an HPLC vial.

Mobile Phase Preparation 100 mM TBuAA (tributylammonium acetate) stock solution: Under a blanket of argon, approximately 450 mL of acetonitrile were added to a 500-mL graduated cylinder. Twelve milliliters of tributylamine and 3 mL of glacial acetic acid were added, and the solution diluted to a final volume of 500 mL with acetonitrile. 100 mM EDTA (ethylenediaminetetraacetic acid) stock solution: 7.3 g of EDTA, 12 mL of tributylamine and approximately 200 mL of bottled HPLC water were transferred to a 250-mL volumetric flask. The mixture was stirred until all the EDTA had dissolved then diluted to a final volume of 250 mL with bottled HPLC water.

Mobile Phase A (5 mM TBuAA, 10% Acetonitrile, 1 uM EDTA): Under a blanket of argon, 50 mL of 100 mM TBuAA stock solution were transferred to a 1-L graduated cylinder. Fifty milliliters of ACN and 10 uL of 100 mM EDTA stock solution were added and the solution diluted to a final volume of 1000 mL with bottled HPLC water.

Mobile Phase B (5 mM TBuAA, 80% Acetonitrile, 1 uM EDTA): Under a blanket of argon, 50 mL of 100 mM TBuAA stock solution were transferred to a 1-L graduated cylinder. Seven hundred and fifty milliliters ACN and 10 uL of 100 mM EDTA stock solution were added and the solution diluted to a final volume of 1000 mL with bottled HPLC water.

Equipment

An Agilent 1100 HPLC-MSD gradient HPLC instrument with variable wavelength UV detector and auto sampler, interfaced to an electrospray mass spectrometer with data processing system was used for the analysis. The parameters shown in Table 8 were used.

TABLE 8

Parameters Used

| Parameter | Setting |
|---|---|
| Mass range | 1643-1943 |
| Scan mode | Negative Polarity |
| Ionization mode | API-ES |
| Needle voltage | 4000 V |
| Nebulizer pressure | 25 ± 5 psig |
| Drying gas flow | 12 L/min |
| Drying gas temperature | 275° C. |
| Fragmentor voltage | 100 V |
| Gain | 2 |
| Threshold | 50 |
| Step size [amu] | 0.1 |
| Data acquisition time | 2-25 minutes |
| Data storage | Full |
| Peak width | 0.12 mins |
| UV detector wavelength | 260 nm (4-nm bandwidth) |
| Reference wavelength | 400 nm (80-nm bandwidth) |

A YMC ODS-AQ HPLC column, 3-um particle size, 200-A pore size, 2×150 mm, held at 50° C. was used for the analysis. The column was eluted under the gradient described in Table 9.

TABLE 9

Column Gradient

| Time (minutes) | Flow Rate (mL/min) | Eluent Composition (%) | |
|---|---|---|---|
| | | A | B |
| 0 | 0.25 | 55 | 45 |
| 22 | 0.25 | 20 | 80 |
| 25 | 0.25 | 20 | 80 |
| 26 | 0.25 | 55 | 45 |
| 35 | 0.25 | 55 | 45 |

Table 2 HPLC gradient used for the analysis of the drug substance

Standard and Sample Analysis

A calibration curve was established by making 10, 20, 25 and 30-uL injections of reference standard. A single 25-uL injection of each sample was made. Two additional 25-uL injections of reference standard, one before and one following the samples were made to confirm proper functioning of the system.

Results

Standards

The UV chromatograms obtained from the three 25-uL injections of reference standard were integrated and the UV purity of each calculated. The relative standard deviation (RSD) of the main UV peak area for the three injections was calculated. The retention time and the most abundant mass of the −4 charge state of the main component was determined for each of these injections. The results are shown in Table 10.

TABLE 10

UV and MS results for 25-uL standard injections

| Standard | UV purity (%) | Peak area Main UV peak area | Retention time of main UV peak | Most abundant mass |
|---|---|---|---|---|
| 25-uL # 1 | 95.17 | 7432.36 | 15.43 | 1793.1 |
| 25-uL # 2 | 95.07 | 7422.33 | 15.407 | 1793.1 |
| 25-uL # 3 | 95.07 | 7444.73 | 15.346 | 1793.2 |

The data in Table 10 showed that the average UV purity for the reference standard injection was within 1% of the 95.2% value assigned. The RSD of the main UV peak area was 0.2% and the retention times of the main UV peak for each injection was between 12 and 22 minutes. The most abundant mass of the −4 four charge state was within 0.2 amu of the calculated value of 1793.0.

Next, the UV peak areas of the main component were plotted against the amount of UV pure material on column for the 10, 20, 25 and 30-uL injections of reference standard. A least-squares line was fit to the data. The extracted ion currents due to the n and $(P=O)_1$ components were summed and plotted against injection volume for the same four injections. A 2-order polynomial equation was fit to this data. The resulting graphs and relationships are shown in FIGS. 6 and 7.

The $R^2$ values of the least-squares line for the UV response and the 2-order polynomial equation used to describe the MS response were 1.0000 and 0.994, respectively. These data, and the data presented in Table 10, indicated the system was functioning correctly.

Sample Analysis

The UV chromatogram of the first injection of the sample is shown in FIG. 8.

The UV chromatogram was integrated and a UV purity of 92.2% assigned. The amounts of early and late eluting impurities were determined at 0.97% and 3.8%, respectively. The average mass spectrum of the main UV peak is displayed in FIG. 9.

The most abundant mass of the −4 charge state of the main component was 1793.2. From this value we calculated the sample had a most abundant mass of 7176.8 amu. This value was within 0.7 amu of that calculated for the 20 nucleotide 5-10-5 2'-O-methoxyethyl gapmer, thus confirming the identity of the sample. Next, the ion currents due to the components that eluted under the main UV peak were extracted and integrated. We took care to avoid extracting and integrating artifact signals due to buffer and salt adducts. The extracted ion currents due to the full-length, fully thioated and $(P=O)_1$ components were summed. To correct for the non-linearity of the mass spectral response, all raw extracted ion currents were converted into effective volumes of injection using the quadratic equation established in FIG. 8. The relative amounts of each species were calculated from these effective volumes of injection. The relative percentages of the full-length, fully thioated and $(P=O)_1$ components were calculated by multiplying their combined effective volume of injection by the decimal fraction of their individual extracted ion currents to the sum of these values. These amounts were then multiplied by the UV purity of the sample to determine the level of each component as percentages of the total sample. Those species present below the LOD of 0.10% were then discarded and the relative amounts of those remaining recalculated. The results of these transformations are shown in Table 11.

TABLE 11

Impurity profile data for the drug substance

| MS Signal | Name of Species | EIC Area | a | b | c | Effective volume of injection | % of UV peak | % of sample | Remove <LOD | Reportable % |
|---|---|---|---|---|---|---|---|---|---|---|
| NA | Full Length and (P=O)1 | 11611333 | −7612.865 | 712645.639 | −11611333.0 | 21.0078 | NA | NA | NA | NA |
| 1793.0 | Full Length | 11361800 | NA | NA | NA | 20.5563 | 94.2005 | 89.7030 | 89.7030 | 90.0898 |
| 1789.0 | $(P=O)_1$ | 249533 | NA | NA | NA | 0.4515 | 2.0689 | 1.9701 | 1.9701 | 1.9786 |
| 1785.0 | $(P=O)_2$ | 14170.2 | −7612.865 | 712645.639 | −14170.2 | 0.0199 | 0.0911 | 0.0868 | ND | ND |
| 1706.8 | n − p(dG) | 5193.16 | −7612.865 | 712645.639 | −5193.2 | 0.0073 | 0.0334 | 0.0318 | ND | ND |
| 1688.3 | n − p(MOE G) | 9782.87 | −7612.865 | 712645.639 | −9782.9 | 0.0137 | 0.0629 | 0.0599 | ND | ND |
| 1694.6 | n − p(MOE Me-C) &/or n − p(MOE Me-U) | 54259.4 | −7612.865 | 712645.639 | −54259.4 | 0.0762 | 0.3492 | 0.3325 | 0.3325 | 0.3340 |
| 1710.8 | n − p(dA) | 2312.07 | −7612.865 | 712645.639 | −2312.1 | 0.0032 | 0.0149 | 0.0142 | ND | ND |
| 1713.1 | n − pT &/or n − p(Me-C) | 26072.2 | −7612.865 | 712645.639 | −26072.2 | 0.0366 | 0.1677 | 0.1597 | 0.1597 | 0.1604 |
| 1692.3 | n − p(MOE A) | 37423.8 | −7612.865 | 712645.639 | −37423.8 | 0.0525 | 0.2408 | 0.2293 | 0.2293 | 0.2303 |
| 1875.3 | n + p(dA) | 27779.5 | −7612.865 | 712645.639 | −27779.5 | 0.0390 | 0.1787 | 0.1702 | 0.1702 | 0.1709 |

TABLE 11-continued

Impurity profile data for the drug substance

| MS Signal | Name of Species | EIC Area | a | b | c | Effective volume of injection | % of UV peak | % of sample | Remove <LOD | Reportable % |
|---|---|---|---|---|---|---|---|---|---|---|
| 1872.9 | n + pT &/or n + p(Me-C) | 8998.22 | −7612.865 | 712645.639 | −8998.2 | 0.0126 | 0.0579 | 0.0551 | ND | ND |
| 1879.3 | n + p(dG) | 16597.2 | −7612.865 | 712645.639 | −16597.2 | 0.0233 | 0.1068 | 0.1017 | 0.1017 | 0.1021 |
| 1755.3 | loss Gua | 0 | −7612.865 | 712645.639 | 0.0 | 0.0000 | 0.0000 | 0.0000 | ND | ND |
| 1759.5 | loss Ade, loss Gua + H2O | 30263 | −7612.865 | 712645.639 | −30263.0 | 0.0425 | 0.1947 | 0.1854 | 0.1854 | 0.1862 |
| 1763.5 | loss Ade + H2O, loss Gua + MeOH | 25091.9 | −7612.865 | 712645.639 | −25091.9 | 0.0352 | 0.1614 | 0.1537 | 0.1537 | 0.1544 |
| 1767.3 | loss Ade + MeOH | 20082.4 | −7612.865 | 712645.639 | −20082.4 | 0.0282 | 0.1292 | 0.1230 | 0.1230 | 0.1235 |
| 1718.7 | 3'-TPT | 10439.2 | −7612.865 | 712645.639 | −10439.2 | 0.0147 | 0.0671 | 0.0639 | ND | ND |
| 1806.3 | CNET | 24251.3 | −7612.865 | 712645.639 | −24251.3 | 0.0340 | 0.1560 | 0.1486 | 0.1486 | 0.1492 |
| 1830.0 | TCE | 3630.73 | −7612.865 | 712645.639 | −3630.7 | 0.0051 | 0.0233 | 0.0222 | ND | ND |
| 1828.0 | EPD | 17228.4 | −7612.865 | 712645.639 | −17228.4 | 0.0242 | 0.1108 | 0.1055 | 0.1055 | 0.1060 |
| 1782.0 | 2'-OCH3 | 72034.4 | −7612.865 | 712645.639 | −72034.4 | 0.1012 | 0.4637 | 0.4416 | 0.4416 | 0.4435 |
| 1766.2 | Unknown (n − 107) | 31719.6 | −7612.865 | 712645.639 | −31719.6 | 0.0445 | 0.2041 | 0.1943 | 0.1943 | 0.1952 |
| 1777.4 | Unknown (n − 62) | 12220.1 | −7612.865 | 712645.639 | −12220.1 | 0.0172 | 0.0786 | 0.0748 | ND | ND |
| 1810.8 | Unknown (n + 71) | 99503.2 | −7612.865 | 712645.639 | −99503.2 | 0.1398 | 0.6408 | 0.6102 | 0.6102 | 0.6128 |
| 1817.5 | Unknown (n + 98) | 30698.1 | −7612.865 | 712645.639 | −30698.1 | 0.0431 | 0.1975 | 0.1881 | 0.1881 | 0.1889 |

The data presented in Table 11 shows the sample contained 90.1% full-length fully thioated material. The data also shows the sample contained a variety of impurities that coeluted with the full-length, fully thioated component. For example, the sample contained approximately 2% of the $(P=O)_1$ component and 0.23% of an impurity lacking a MOE A nucleotide [n-p(MOE A)]. The total amount of the 20 nucleotide 5-10-5 2'-O-methoxyethyl gapmer including $(P=O)_1$ in the sample was 90.1%+2.0%=92.1%.

To calculate a weight based assay for the sample, we summed the full-length, fully thioated and $(P=O)_1$ content of the sample (90.1% and 2.0%) and divided this sum by the UV purity (92.2%) to give a mass spectral purity for the sample of 97.7%. We calculated the concentration of UV pure material in solution by plugging the UV areas of the main peaks of both sample injections into the least-squares line formula derived in FIG. 6. The concentration of UV pure material in solution was then multiplied by the mass spectral purity to give the concentration of 20 nucleotide 5-10-5 2'-O-methoxyethyl gapmer including $(P=O)_1$ in solution. These calculations are shown in Table 12.

TABLE 12

Concentration of the drug substance including $(P=O)_1$ in solution

| Sample | UV area of main peak | Concentration of UV pure material in solution (ug/uL)[1] | Mass spectral purity | Concentration of UV pure material in solution (ug/uL) |
|---|---|---|---|---|
| Sample 1 | 6447.16 | 0.0857 | 97.7% | 0.0837 |
| Sample 2 | 6415.70 | 0.0853 | | 0.0833 |

[1]Determined from least square equation in FIG. 6

These values were then multiplied by the total sample volume of 250 mL to give the total amount of the drug substance including $(P=O)_1$ in the sample. To calculate the % assay value, these estimates were divided by the sample weights (corrected for water, salt and solvent content). An average assay value from the two replicates of 94.3% was determined.

We claim:

1. A method comprising:
   introducing a sample comprising a plurality of oligonucleotides into an ion pair high performance liquid chromatography column having a buffered mobile phase and allowing at least a portion of the oligonucleotides to separate;
   allowing the oligonucleotides to elute from the column; and
   introducing the oligonucleotides into a mass spectrometer and quantifying at least a portion of the oligonucleotides by mass spectrometry;
   wherein at least a portion of the oligonucleotides are co-eluting oligonucleotides; and
   wherein the buffered mobile phase causes at least 50 mole percent of co-eluting oligonucleotides to have the same charge when they enter the mass spectrometer.

2. The method of claim 1 additionally comprising detecting oligonucleotides with UV detection before they enter the mass spectrometer.

3. The method of claim 2 wherein oligonucleotides differing by 20 mass percent or less are quantified by mass spectrometry and those differing by more than 20 mass percent are quantified by their UV spectra.

4. The method of claim 2 wherein co-eluting oligonucleotides are quantified by mass spectrometry, wherein the quantification comprises utilization of a calibration curve obtained by a plot of mass spectral response versus the amount of a sample oligonucleotide injected into the mass spectrometer to determine the amount of the individual oligonucleotides.

5. The method of claim 4, wherein the co-eluting oligonucleotides comprise a target oligonucleotide, and one or more of the impurities selected from the target oligonucleotide missing one nucleotide, the target oligonucleotide missing the one nucleoside, the target oligonucleotide missing one purine base with or without the addition of methanol or water, the target oligonucleotide missing one pyrimidine base with or without the addition of methanol or water, the target oligonucleotide containing an additional nucleotide, the target oligonucleotide containing an additional ethylenephosphorothioate group, the target oligonucleotide containing an additional trichlorethanol group or the target oligonucleotide containing an additional cyanoethyl group.

6. The method of claim 1, wherein the buffered mobile phase has a pH from about 6 to about 8.

7. The method of claim 1, wherein the buffered mobile phase comprises a bulky amine and an acid.

8. The method of claim 7, wherein the bulky amine is a trialkylamine.

9. The method of claim 8, wherein the trialkylamine is selected from tripropylamine, tributylamine, tripentylamine, trihexylamine, dimethylhexylamine, dimethyloctylamine, or diethylbutylamine.

10. The method of claim 7, wherein the bulky amine is tributylamine.

11. The method of claim 7, wherein the acid is selected from acetic acid, formic acid, propionic acid, trifluoracetic acid or carbonic acid.

12. The method of claim 7, wherein the acid is acetic acid.

13. The method of claim 1, wherein at least 50 mole percent of the co-eluting oligonucleotides are in the −1, −2, −3, −4, −5, or −6 charge state.

14. The method of claim 1, wherein at least 50 mole percent of the co-eluting oligonucleotides are in the −3, −4, or −5 charge state.

15. The method of claim 1, wherein at least 70 mole percent of the co-eluting oligonucleotides are in the −4 charge state.

16. The method of claim 1, wherein the oligonucleotides comprise single strand or double strand oligonucleotides.

17. The method of claim 1, wherein at least one oligonucleotide comprises at least one chemical modification.

18. The method of claim 17, wherein the chemical modification is at least one of a modified base, a modified sugar, a modified internucleoside linkage or a conjugate group linked to the oligonucleotide.

19. The method of claim 1, wherein the co-eluting oligonucleotides comprise 12 to 30, 15-25 or 19 to 21 nucleobases.

20. The method of claim 1, wherein the co-eluting oligonucleotides comprise 19 to 21 nucleobases.

21. The method of claim 1 wherein at least one oligonucleotide is a drug substance.

22. The method of claim 1 wherein the quantification of the co-eluting oligonucleotides uses a common calibration curve.

* * * * *